United States Patent [19]

Christ

[11] Patent Number: 4,991,592

[45] Date of Patent: Feb. 12, 1991

[54] DEVICE FOR OBTAINING TISSUE SAMPLE IN PERFORMING A BIOPSY

[76] Inventor: Howard N. Christ, 291 Cedar Ave., Islip, N.Y. 11751

[21] Appl. No.: 445,363

[22] Filed: Dec. 4, 1989

[51] Int. Cl.⁵ .............................................. A61B 10/00
[52] U.S. Cl. ..................................... 128/754; 604/116
[58] Field of Search ............... 128/749, 751, 754, 879, 128/880, 399, 402, 82,1, 642, 662.05; 604/116, 171, 263, 280

[56] References Cited

U.S. PATENT DOCUMENTS

| | | | |
|---|---|---|---|
| 2,880,724 | 4/1959 | Velarde | 604/116 |
| 3,595,217 | 7/1971 | Rheinfrank | 128/754 |
| 4,327,744 | 5/1982 | Smith | 128/749 |
| 4,542,747 | 9/1985 | Zurinski et al. | 128/662.05 |
| 4,733,661 | 3/1988 | Palestrant | 604/116 |

FOREIGN PATENT DOCUMENTS 0461457 6/1928 Fed. Rep. of Germany ...... 604/116

Primary Examiner—Max Hindenburg

Attorney, Agent, or Firm—Edward H. Loveman

[57] ABSTRACT

This device employs an elastic, thin walled tubular member which can be a finger receiving and enclosing portion of a rubber glove or a rubber finger cot. The tubular member has a closed end for engaging the wearer's fingertip and an open end through which extends a flexible tube having a beveled end secured to the inner side of the closed end of the tubular member. The tube extends through a palmar portion of the glove or along the palm of the wearer of the cot, where an external portion of the tube is exposed for insertion of a biopsy needle. The tube has an axial passage through which a biopsy needle can be guided to pierce the closed end of the tubular member and a site inside a body cavity being palpated by the wearer, while the needle pierces the site to remove a sample of tissue to be examined after the needle is withdrawn from the tube. The external portion of the tube can be grasped by other fingers of the wearer's hand to stabilize the tube against movement while the biopsy needle is being inserted and removed by the wearer's other hand.

8 Claims, 2 Drawing Sheets

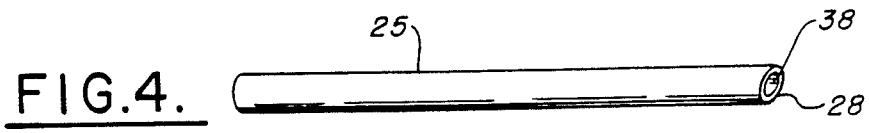
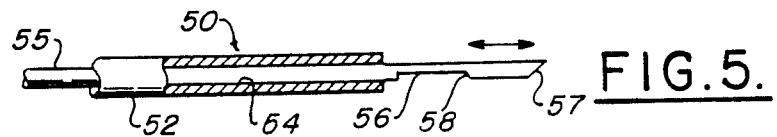
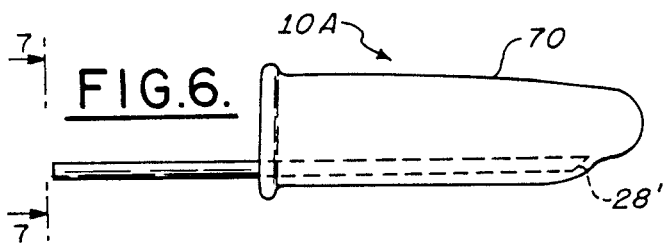
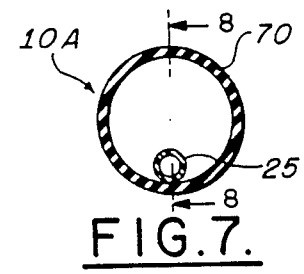
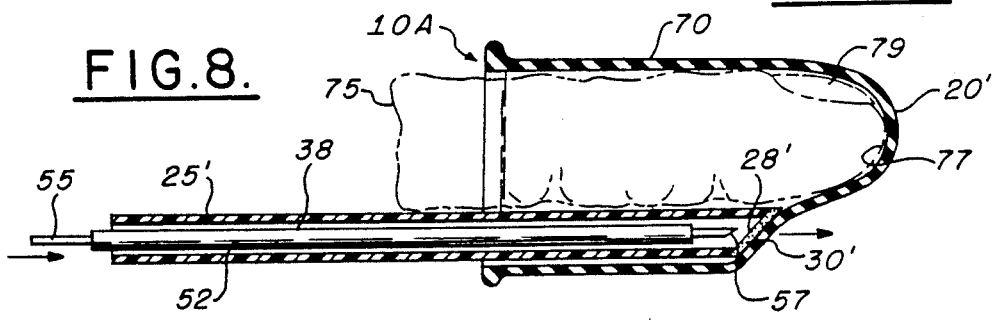
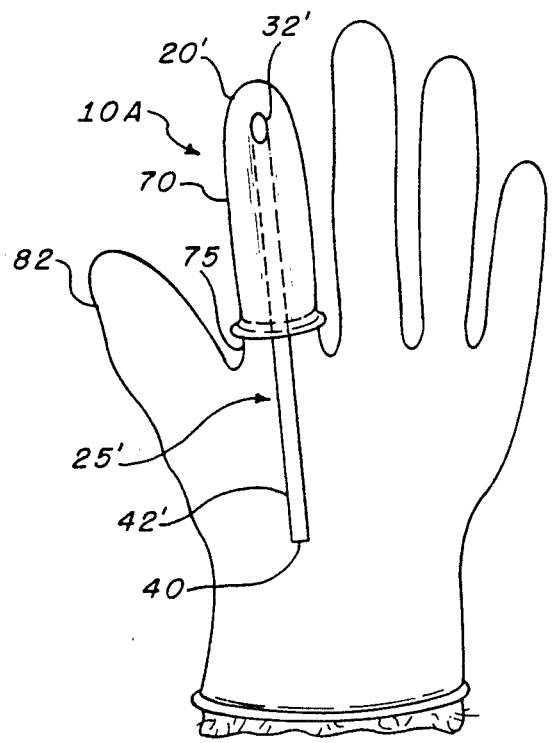

DEVICE FOR OBTAINING TISSUE SAMPLE IN PERFORMING A BIOPSY

BACKGROUND OF THE INVENTION

1. Field of the Invention

This invention relates to devices used to obtain samples of organ tissue in performing a biopsy, and more particularly the invention involves a device which facilitates palpating an area of a body organ, with means for guiding biopsy needle to the particular area being palpated.

2. Description of the Prior Art

Heretofore biopsy needles have been inserted into organs in body cavities with no assurance that the precise desired area has been located, from which area a tissue sample is to be extracted. Sonogram equipment is available which enables a surgeon to insert a biopsy needle into an internal organ while observing the needle placement on the sonogram screen. Such equipment can be used for a limited number of organs; but a principal disadvantage is that such equipment is not generally available in most physician's offices. More importantly, many times the sonogram display is unclear and it is important that the surgeon or diagnostician physically feel the area of interest by actual palpation of the organ. In many situations, such as examination of the prostate gland and other organs transrectally, transvaginally, intra-abdominally, etc., a need had existed for means to enable palpating a particular area of an internal organ and therefore simultaneously guiding a biopsy needle precisely to the palpated area while the surgeon's palpating finger is placed in that area.

SUMMARY OF THE INVENTION

It is therefore a principal object of the present invention to provide a device which enables a surgeon, diagnostician, technician, etc, palpate a body organ, with a tube disposed adjacent to the palpating finger to guide a biopsy needle precisely to the point or area being palpated.

According to the invention there is provided an elastic rubber or plastic glove, with a flexible plastic tube extending along and inside the index finger of the glove. The tube extends to within four to six millimeters of the closed tip end of the finger. When a surgeon inserts his hand into the glove, his index finger is snugly enclosed by the elastic tubular index finger portion while the tube laterally abuts the underside of his index finger. The tube is beveled at its inner end. The oval end is cemented to the tip of the tubular index finger portion of the glove. The other end of the tube extends outwardly to and through the palmar area of the glove. A biopsy needle may then be inserted through the tube to pierce the closed end of the finger enclosing portion of the glove, and the particular area of the body organ being palpated by the surgeon's finger. The other fingers of the surgeon's hand can grasp the tube to hold it stably while the surgeon inserts the biopsy needle into the plastic tube with his other hand. Since the tube is located at the palmar side of the glove, it may be necessary to provide right and left hand gloves equipped with guide tubes as described.

In a modification of the invention the plastic guide tube can be inserted axially into an elastic finger cot, with the oval beveled end of the tube cemented at the closed end of the cot. The finger cot can then be rolled down over any desired finger on a gloved or ungloved surgeon's hand, with the outer end of the tube extending to the palm of the hand or beyond. The cot can be used on right or left hands. The other fingers of the hand holding the cot can grasp the tube to stabilize it while the biopsy needle is inserted to pierce the end of the cot and the palpated area of the organ from which a tissue sample is the be extracted.

These and other objects and many of the attendant advantages of this invention will be readily appreciated as the same becomes better understood by reference to the following detailed description when considered in connection with the accompanying drawings in which:

BRIEF DESCRIPTION OF THE DRAWINGS

FIG. 4 is an oblique view of the guide tube;

FIG. 5 is an enlarged side view of a portion of a two-part biopsy needle assembly which can be used with the device, a portion of the cannula of the needle being broken away;

FIG. 6 is a side view of a device embodying a modification of the invention in which an elastic finger cot retains a guide tube for a biopsy needle;

FIG. 7 is an enlarged end view taken along line 7—7 of FIG. 6;

FIG. 8 is a further enlarged axial sectional view taken along line 8—8 through the finger cot and guide tube, with a biopsy needle shown inside the tube; and FIG. 9 is a plan view of the device of FIGS. 6-8, shown on a gloved hand.

Figure 1:
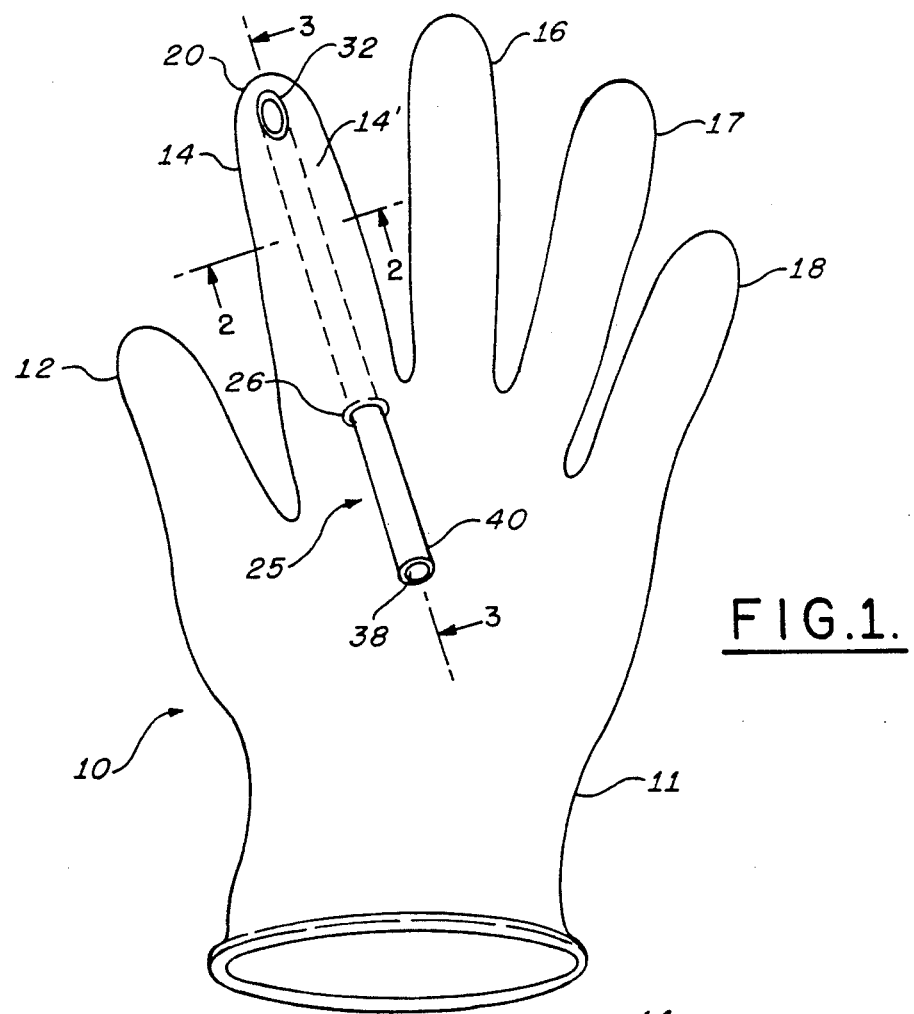
FIG. 1 is a plan view of a device embodying the invention employing a glove shown palmar side up.
Figure 2:
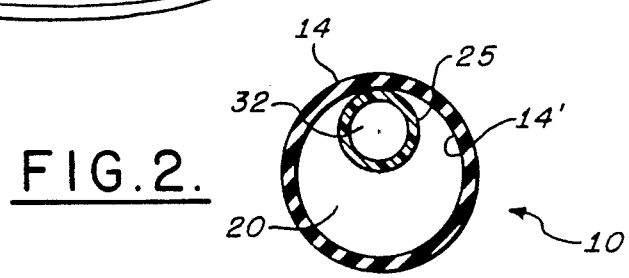
FIG. 2 is an enlarged cross sectional view taken along line 2—2 of FIG. 1, through a tubular finger of the glove.
Figure 3:
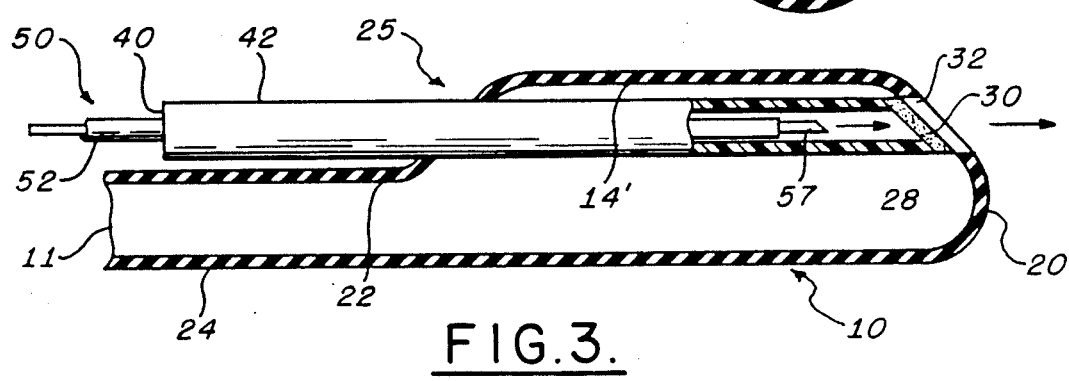
FIG. 3 is an enlarged fragmentary longitudinal sectional view of the glove taken along line 3—3 of FIG. 1 through the glove and guide tube, with a biopsy needle shown inside the tube.

Referring now to the drawings wherein like reference characters designated like or corresponding parts throughout, there is illustrated in FIGS. 1, 2, and 3 a device generally designated as reference numeral 10 embodying the invention which comprises a surgical type glove 11 made of elastic rubber or plastic material. The glove 11 has a tubular thumb receiving portion 12, a tubular index finger receiving portion 14, and three other finger receiving tubular portions 16, 17 and 18, all closed at their respective ends 20. The thumb portion 12 and the finger receiving portions 14, 16, 17 and 18 are integral with a palm portion 22 at one side of the glove 11 and a back portion 24 at the other side of the glove 11. A flexible plastic tube 25 extends through an aperture 26 in the palmar portion 22. The tube 25 extends axially along the palmar portion 22 inside the glove 11 and along an adjoining integral wall 14' of the index finger receiving and enclosing portion 14 to approximately 4-6 mm of the tip of the index portion 14. The tube 25 has a beveled open end 28 as best shown in FIGS. 3 and 4. A tube end 28 is secured by a cement layer 30 to the inner side of the closed end 20 of the tubular index portion 14. A thin, flat oval frangible diaphragm 32 is defined by the oval end 28 of the tube 25 at closed end 20. The axial passage 38 in tube 25 is open between inner end 28 and outer end 40.

The outer end portion 42 of the tube 25 extends axially longitudinally of palmar portion 22 outside the glove 11. The outer end 40 of the tube is open so that a biopsy needle assembly 50 can be inserted into and along axial passage 38.

The tube 25 is located adjacent to the thumb receiving and enclosing portion 12, so that the tube 25 can be grasped by the thumb and fingers of the surgeon or other person wearing the glove 11 to stabilize the tube 25 against axial, lateral and rotational movement in index finger receiving portion 14. The wearer's index finger is free to palpate a portion of an internal organ or other site in a body cavity such as rectum, mouth, vagina, etc. If the surgeon has made an incision in a patient's body, the surgeon wearing the glove can insert his index finger in the incision and palpate the tissue where the biopsy needle is to be inserted. Thus the biopsy needle can be inserted even though the surgeon cannot see the site where the needle is being inserted. The tube 25 guides the movement of the needle while the tip of the surgeon's finger adjacent the end of the tube feels and directs the needle to the exact point desired.

FIG. 5 shows part of a biopsy needle assembly 50 which may be used with the device embodying the invention. The assembly 50 has a long thin cannula 52 with a narrow bore 54. Slidably inserted in the cannula 52 is a needle 55 which has a sharp pointed end 57 and may be beveled at one side. Close to the pointed end 57 is a notch 56 having slanted ends 58, 59. The tissue to be extracted by the needle is caught in the notch 56 and withdrawn with the needle 55 and the cannula 52 from the guide tube 25. The sharp pointed end of the needle 55 facilitates piercing the diaphragm 32 at the end of the tube 25. The piercing of the body organ by the needle 55 is quick and precise and causes a minimum of damage to tissue surrounding the puncture. The entire operation is performed accurately with minimum discomfort and trauma to the patient.

The glove 11 as shown in FIG. 1 is a left handed glove to receive the left hand of the surgeon or other person using the device 10, because the thumb receiving portion 12 is immediately to the left of the index finger receiving portion 14 at the palmar side 22 of the glove 11. If the device 10 is required for right hand use, then a right handed glove will have to be provided with the tube 25 in the index finger receiving portion 14. The thumb receiving portion 12 will then be to the right of the index finger receiving portion 14. The thumb receiving portion 12 will then be to the right of the index finger receiving portion 14 at the palmar side 22 of the glove 11. In other words, the right-hand glove will be a mirror image of the left-hand glove shown in FIG. 1.

FIGS. 6-9 shown another form of the invention in which the device 10A comprises a tubular member holding a flexible tube 25' in a finger cot 70 which is made of elastic rubber or plastic material and has an axial length as long as or slightly shorter than the length of a finger 75 to be inserted into the cot 70. The cot 70 has a closed end 20' which engages snugly around a tip 77 of the finger 75 shown in dotted lines in FIG. 8. An oval beveled end 28' of the tube 25' is secured by cement 30' to the inside of a closed end 20' of the cot 70. A flat diaphragm 32' is located at an end 28' of the tube 25' where it can readily be pierced by the sharp end 57 of the biopsy needle 55 slidable in the cannula 52 of assembly 50. The cot 70 can be placed on a bare finger, but preferably it will be placed on the index finger 75 of a surgeon's hand enclosed in a glove 82, as shown in FIG. 9. The cot 70 can be placed on any finger of either right of left hand. In all cases the tube 25' will extend along the finger with the end 28' facing away from the finger tip 77 but located so that the needle tip 57 will pierce the oval, flat diaphragm 32' close to the side of the fingertip 77 opposite the nail 79. The outer end portion 42' of the tube 25' will always be located along the palm of the surgeon's hand, so that the tube 25' can be grasped by other fingers and the thumb of the hand for stabilizing the tube against movement in any direction when the biopsy needle assembly 50 is inserted through the end 40' into the passage 38' of the tube 25'.

The device 10 or 10A employing glove 11 or cot 70 can be made in various sizes and of various materials depending on specifications for any particular application. The device in any form is intended to be discarded after a single use. It can be packed flat in a sterilized package and occupies minimum storage space. It is inexpensive to manufacture, yet it performs vital functions when a biopsy of a site inside a body cavity is to be performed.

It should be understood that the foregoing relates to only a preferred embodiment of the invention which has been by way of example only, and that it is intended to cover all changes and modifications of the example of the invention herein chosen for the purpose of the disclosure, which do not constitute departures form the spirit and scope of the invention.

What is claimed is:

1. A device for obtaining a sample of tissue from a body organ in a body cavity in performing a biopsy, comprising:

an elastic, thin walled, tubular member for enclosing a person's finger, said member having an open end for insertion of said person's fingertip, and having a closed end snugly engageable around said fingertip to enable palpation by said fingertip of a particular area of said organ; and a flexible tube longer than said tubular member extending axially inside said member along one side thereof, said tube having an inner end secured at and inside said closed end of said member, and having a free outer end disposed beyond said open end of said member to receive a biopsy needle, with said inner end of said tube being beveled to face said one side of said member and to face away from said fingertip; and said tube having an axial passage for guiding said biopsy needle therethrough to pierce said closed end of said tubular member as close as possible to said fingertip and said palpated area of said organ adjacent to said fingertip, to obtain a sample of tissue thereat.

2. A device as claimed in claim 1, wherein said inner end of said tube is cemented to said closed end of said tubular member to define an oval flat diaphragm which can be readily pierced by said needle when inserted through said passage in said tube.

3. A device as claimed in claim 2, wherein said tube is long enough to extend over the palmer area of said person's hand adjacent to said finger in said tubular member to permit said tube to be grasped and stabilized by other fingers of said person's hand, while said biopsy needle is inserted in said tube, and while said needle is being withdrawn from said tube with said sample of tissue.

4. A device as defined in claim 3, wherein said tubular member is a finger cot engageable upon any selected finger of either hand of said person.

5. A device as defined in claim 3, wherein said tubular member is part of an elastic glove having finger and thumb enclosing portions with closed ends for enclosing palm, thumb, and fingers of said person's hand, and wherein said outer end of said tube extends through a palmer portion of said glove to terminate outside said glove for insertion of said biopsy needle into said tube.

6. A device as claimed in claim 5, wherein said tubular member is an index finger receiving portion of said glove adjacent to said thumb receiving portion, so that said thumb and other fingers of said person can grasp said tube to stabilize the same while said biopsy needle is being inserted in and removed from said tube.

7. A device for obtaining a sample of tissue extracted from a body organ in a body cavity, comprising:
- an elastic glove having spaced palm and back portions integral with tubular finger and thumb receiving and enclosing portions, said other portions having closed ends; and
- a flexible tube extending axially of and within one of said finger receiving portions of said glove, said tube having an inner end secured inside a closed end of said one finger receiving portion, said inner end of said tube being beveled to face one side of said finger receiving portion and inclined to the tip of said one finger said tube having an outer end extending through said palm portion where said tube can be grasped by fingers and thumb of a person wearing said glove to stabilize said tube, said tube having an axial passage for guiding a biopsy needle therethrough to pierce said closed end of said one finger receiving portion and a site in a body cavity while said one finger palpates said site to insure that said needle pierce said site precisely at a desired point to extract said sample of tissue.

8. A device as claimed in claim 7, wherein said inner end of said tube is cemented to said closed end of said one finger receiving portion to define an oval flat diaphragm which can readily be pierced by said needle when inserted through said passage in said tube.

* * * * *